(12) United States Patent
Cole et al.

(10) Patent No.: US 6,673,358 B1
(45) Date of Patent: Jan. 6, 2004

(54) WET WIPES CONTAINING A MONO ALKYL PHOSPHATE

(75) Inventors: Douglas Bryan Cole, Appleton, WI (US); Katherine Denise Stahl, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/464,418

(22) Filed: Dec. 16, 1999

(51) Int. Cl.[7] .................. A01N 25/34; A01N 59/00; A61K 33/00; A61K 31/66
(52) U.S. Cl. .................. 424/404; 424/722; 514/109; 514/141
(58) Field of Search .................. 424/404; 514/722, 514/109, 141

(56) References Cited

U.S. PATENT DOCUMENTS

| | | | |
|---|---|---|---|
| 4,100,324 A | 7/1978 | Anderson et al. | 442/344 |
| 4,139,485 A | 2/1979 | Imokawa et al. | 510/236 |
| 4,369,134 A | 1/1983 | Deguchi et al. | 510/404 |
| 4,465,613 A | 8/1984 | Carter | 510/347 |
| 4,493,782 A | 1/1985 | Williamson | 510/467 |
| 4,504,409 A | 3/1985 | Tsutsumi et al. | 516/57 |
| 4,707,292 A | 11/1987 | Sano et al. | 510/404 |
| 4,753,749 A | 6/1988 | McIntosh | 510/382 |
| 4,830,764 A | 5/1989 | Wiedemann | 435/233 |
| 4,836,949 A | 6/1989 | Klajnscek | 510/337 |
| 4,912,245 A | 3/1990 | Girardeau et al. | 558/113 |
| 4,931,201 A | 6/1990 | Julemont | 15/104.93 |
| 4,935,232 A * | 6/1990 | McIntosh | 424/78 |
| 4,948,585 A * | 8/1990 | Schlein | 424/404 |
| 4,968,450 A | 11/1990 | Kamegai et al. | 510/413 |
| 5,015,471 A | 5/1991 | Birtwistle et al. | 424/70.19 |
| 5,071,585 A | 12/1991 | Matsunaga et al. | 510/426 |
| 5,078,991 A | 1/1992 | Birtwistle et al. | 510/122 |
| 5,085,854 A | 2/1992 | Fukuda et al. | 424/63 |
| 5,093,112 A | 3/1992 | Birtwistle et al. | 424/70.23 |
| 5,124,077 A | 6/1992 | Kajihara et al. | 510/130 |
| 5,334,387 A | 8/1994 | Haugk | 510/137 |
| 5,550,274 A | 8/1996 | Reierson | 558/110 |
| 5,554,781 A | 9/1996 | Reierson | 558/110 |
| 6,008,177 A * | 12/1999 | Sata et al. | 510/391 |

FOREIGN PATENT DOCUMENTS

| | | |
|---|---|---|
| CA | 1087956 | 10/1980 |
| CA | 1334273 C | 2/1995 |
| CA | 2003839 C | 8/1995 |
| CA | 2003842 C | 8/1995 |
| CA | 1337106 C | 9/1995 |
| CA | 2003841 C | 10/1995 |
| EP | 0 442 701 A2 | 8/1991 |
| EP | 0 675 076 A3 | 10/1995 |
| GB | 2 283 755 A | 5/1995 |
| WO | WO 97/09033 A1 | 3/1997 |

OTHER PUBLICATIONS

Wenninger, John A., and G.N. McEwen, Jr., editors, International Cosmetic Ingredient Dictionary and Handbook, Seventh Edition, 1997, vol. 1, pp. xix–xx, and vol. 2, pp. 1262, 1282, and 1287.

* cited by examiner

Primary Examiner—Theodore J. Criares
(74) Attorney, Agent, or Firm—Michael J. Bendel; Gregory E. Croft

(57) ABSTRACT

Wet wipes impregnated with a solution which includes a mono alkyl phosphate are described. In particular, the solution in the wet wipes includes a phosphate ester surfactant which includes a mono alkyl phosphate having the following structural formula:

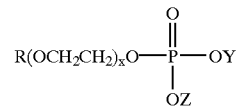

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine. Such wet wipes have improved tactile properties and cleaning efficacy without excessive skin irritation or foaming when compared to conventional wet wipes.

53 Claims, No Drawings

WET WIPES CONTAINING A MONO ALKYL PHOSPHATE

BACKGROUND OF THE INVENTION

1. Field of the Invention

The present invention relates to fibrous sheet materials which are premoistened with a solution for improved cleansing without excessive skin irritation. The invention particularly concerns wet wipes, such as baby wipes, which include a mono alkyl phosphate.

2. Description of the Related Art

Wet wipes are well known commercial consumer products which have been available in many forms. Perhaps the most common form of wet wipes has been a stack of moistened sheets which have been packaged in a plastic container. The wet wipes have been made from a variety of materials which have been moistened with a variety of suitable wiping solutions. Typically, the wet wipes have been available in either folded or unfolded configurations. For example, stacks of wet wipes have been available wherein each of the wet wipes in the stack has been arranged in a folded configuration such as a c-folded, z-folded or quarter-folded configuration as are well known to those skilled in the art. Each folded wet wipe has also been interfolded with the wet wipes immediately above and below in the stack of wet wipes. In an alternative configuration, the wet wipes have been in the form of continuous webs of material which include perforations to separate the individual wet wipes and which are wound into rolls and packaged in plastic containers. Such wet wipes have been used for baby wipes, hand wipes, household cleaning wipes, industrial wipes and the like.

The solutions incorporated into conventional wet wipes have usually included a number of ingredients intended to enhance or impart particular properties to the wipe. These properties have related to, for example, cleaning efficacy, fragrance, medication, reduced irritation, skin health, aesthetics of the product and the like. For baby wipes in particular, a solution providing a gentle soothing feeling without excessive irritation or foam while maintaining cleaning and antimicrobial efficacy is highly desirable for product performance. Suitable ingredients used to provide such properties have included water, emollients, surfactants, preservatives, chelating agents, pH buffers or combinations thereof. The solutions have also contained lotions and/or medicaments.

However, the conventional solutions and, in particular, the surfactants in such solutions for wet wipes have not been completely satisfactory. For example, to reduce the level of skin irritation, conventional wet wipe solutions have included amphoteric surfactants which generally cause little or no skin irritation. Such amphoteric surfactants have included sodium cocoamphoacetate and disodium cocoamphodiacetate. However, such amphoteric surfactants have typically not exhibited the high levels of cleaning efficacy associated with other surfactants such as anionic surfactants. Such amphoteric surfactants typically have also not provided the optimum silky feeling to the skin which is desired by consumers.

On the other hand, anionic surfactants, while exhibiting such cleaning efficacy, have generally caused excessive skin irritation such as dryness and scaling and, as a result, have not been suitable for use in wet wipe applications. The high level of skin irritation caused by such surfactants is particularly undesirable in baby wipe applications due to the tenderness of the infants skin. Moreover, most anionic surfactants are suitable for detergent compositions due to their high levels of foaming and detersive activity. However, such foaming is generally undesirable in wet wipe applications and, in particular, in baby wipe applications. Consumers who use wet wipes prefer that the solution from the wet wipes not leave any soapy or bubbly residue on the surface of the skin since the solution is usually not wiped off the skin after the wet wipe is used.

Accordingly, it remains desirable to provide solutions for wet wipes which include surfactants which exhibit improved cleaning efficacy while not causing excessive skin irritation or foaming.

SUMMARY OF THE INVENTION

In response to the difficulties and problems discussed above, new wet wipes which have improved solutions have been discovered.

In one aspect, the present invention relates to a wet wipe which includes a fibrous sheet material and a solution which includes from about 0.01 to about 10 weight percent based on a total weight of the solution of a phosphate ester surfactant. The phosphate ester surfactant includes a mono alkyl phosphate having the following structural formula:

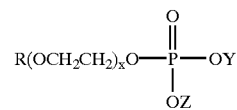

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine.

In another aspect, the present invention relates to a wet wipe comprising a fibrous sheet material and a solution which includes from about 0.01 to about 10 weight percent based on a total weight of the solution of a phosphate ester surfactant. The phosphate ester surfactant includes from about 50 to about 100 weight percent of a mono alkyl phosphate having the following structural formula:

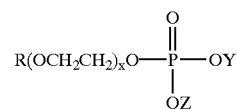

and from about 0 to about 50 weight percent of a dialkyl phosphate having the following structural formula:

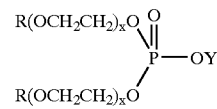

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine.

In yet another aspect, the present invention relates to a wet wipe which includes a fibrous sheet material and a solution. The solution includes from about 0.01 to about 10 weight percent based on a total weight of the solution of a phosphate ester surfactant which includes a mono alkyl phosphate having the following structural formula:

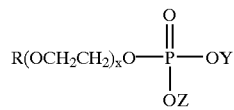

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine. The solution further includes from about 0.01 to about 5.0 weight percent based on a total weight of the solution of a diethanolamide.

The present invention, in its various aspects, advantageously relates to wet wipes which, when compared to conventional wet wipes, have improved cleaning efficacy without excessive skin irritation or foaming. Moreover, the present invention provides solutions for wet wipes which leave a lubricious, silky feeling to the skin during after application.

DETAILED DESCRIPTION OF THE INVENTION

The present invention relates to fibrous materials and, in particular, wet wipes which have improved cleaning efficacy without, excessive skin irritation or foaming. The wet wipes of the present invention can be used for baby wipes, hand wipes, face wipes, cosmetic wipes, household wipes, industrial wipes and the like. Such wet wipes are generally folded and arranged in a stacked configuration inside a suitable container for consumer sale.

Materials suitable for such wet wipes are well known to those skilled in the art. The wet wipes are typically made from fibrous sheet materials which may be woven or nonwoven. For example, the wet wipes of the present invention may include nonwoven fibrous sheet materials which include meltblown, coform, air-laid, bonded-carded web materials, hydroentangled materials, combinations thereof and the like. Such materials can comprise synthetic or natural fibers or combinations thereof. Typically, the wet wipes define a basis weight of from about 25 to about 120 grams per square meter and desirably from about 40 to about 90 grams per square meter.

In a particular aspect, the wet wipes of the present invention comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324 to Anderson et al. which issued Jul. 11, 1978, and which is herein incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending on the desired characteristics of the wet wipes. For example, the coform basesheet may comprise from about 20 to about 100 weight percent, desirably from about 20 to about 60 weight percent, and more desirably from about 30 to about 40 weight percent of polymeric microfibers based on the dry weight of the coform basesheet being used to provide the wet wipes.

Alternatively, the wet wipes of the present invention can comprise a composite which includes multiple layers of materials. For example, the wet wipes may include a three layer composite which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

The individual wet wipes are generally arranged in a folded configuration. Such folded configurations are well known to those skilled in the art and include c-folded, z-folded, quarter-folded configurations and the like. Each wet wipe may also be interfolded with the wet wipes immediately above and below in the stack of wet wipes. The wet wipes generally define an unfolded width and an unfolded length. The wet wipes may have any suitable unfolded width and length. For example, the wet wipes may have an unfolded length of from about 2.0 to about 80.0 centimeters and an unfolded width of from about 2.0 to about 80.0 centimeters.

The wet wipes of the different aspects of the present invention also contain a solution which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping. In a particular aspect, wherein the wet wipes are made from a coform material comprising from about 30 to about 40 weight percent polymeric microfibers based on the dry weight of the wipe, the amount of solution contained within the wet wipe is from about 300 to about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container.

To provide improved improved tactile properties and cleaning efficacy without excessive foaming or skin irritation, the solution in the wet wipes of the present invention includes a phosphate ester surfactant. In particular, the solution in the wet wipes of the present invention includes a phosphate ester surfactant which includes a mono alkyl phosphate having the following structural formula:

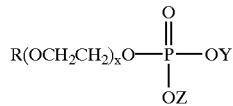

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine.

The phosphate ester surfactant in the solution for the wet wipes of the present invention may further include a dialkyl phosphate having the following structural formula:

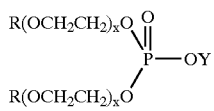

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine.

To provide the improved tactile and cleansing properties to the wet wipe of the present invention without excessive foaming or skin irritation, the weight ratio of the mono alkyl phosphate to the dialkyl phosphate in the solution should be at least about 50:50 and desirably at least about 80:20. Solutions having a mono alkyl phosphate to dialkyl phosphate ratio less than those described above are generally undesirable because of undesirable tactile properties such as tackiness and loss of silky after feel, reduced detersive activity and increased skin irritation.

The saturated or unsaturated hydrocarbon groups having an average of from 8 to 22 carbon atoms can be straight chain, branched or alicyclic hydrocarbons as are known to those skilled in the art. Desirably, the saturated or unsaturated hydrocarbon groups have an average of from 10 to 18 carbon atoms for improved cleaning. For example, in a particular embodiment the saturated or unsaturated hydrocarbon groups have an average of 12 carbon atoms and are derived from coconut oil.

Alkali metals and amines for use in the present invention are known to those skilled in the art. For example, suitable alkali metals include, for example, lithium, sodium, potassium, and the like. Suitable amines include dimethylmonoethanolamine, methyidiethanolamine, trimethylamine, triethylamine, dibutylamine, butyldimethylamine, monoethanloamine, diethanolamine, triethanolamine, isopropyldimethylamine and isopropylethanolamine.

The phosphate ester surfactant in the wet wipes of the present invention may also include ethylene oxide. As set forth above, the phosphate ester surfactant may include from 0 to about 20 moles of ethoxylation. Desirably, the phosphate ester includes from 0 to about 8 moles of ethoxylation and more desirably from 0 to about 3 moles of ethoxylation. The higher the level of ethoxylation, the more hydrophilic the surfactant becomes which can be undesirable. The phosphate ester surfactant in the wet wipes of the present invention may otherwise include propylene oxide. For example, the phosphate ester surfactant may include from 0 to about 20 and desirably from 0 to about 8 moles of propoxylation.

Suitable phosphate ester surfactants for use in the present invention and methods of making the same are described in U.S. Pat. No. 4,139,485 issued Feb. 13, 1979, to Imokawa et al.; U.S. Pat. No. 5,124,077 issued Jun. 23, 1992, to Kajihara et al.; U.S. Pat. No. 5,550,274 issued Aug. 27, 1996 to Reierson: U.S. Pat. No. 5,554,781 issued Sep. 10, 1996 to Reierson; and European Pat. Application No. 0 675 076 published Oct. 4, 1995 in the name of Reierson, the disclosures of which are herein incorporated by reference. For example, suitable phosphate ester surfactants can include sodium mono lauryl phosphate, sodium dilauryl phosphate, potassium mono lauryl phosphate, potassium dilauryl phosphate, diethanolamine mono lauryl phosphate, diethanolamine dilauryl phosphate, triethanolamine mono lauryl phosphate, triethanolamine dilauryl phosphate, sodium mono coco phosphate, sodium dicoco phosphate, potassium mono coco phosphate, potassium dicoco phosphate, triethanolamine mono coco phosphate, triethanolamine dicoco phosphate, sodium mono capric phosphate, sodium dicapric phosphate, potassium mono capric phosphate, potassium dicapric phosphate, triethanolamine mono capric phosphate, triethanolamine dicapric phosphate, and the like and combinations thereof. In a particular embodiment, a suitable phosphate ester surfactant is a potassium laureth mono alkyl phosphate surfactant commercially available from Rhone-Poulenc, a business having offices located in Cranbury, N.J., under the trade designation RHODAFAC.

The solution may include any amount of the phosphate ester surfactant which provides the desired properties. In a particular embodiment, the solution includes from about 0.01 to about 10 weight percent and desirably from about 0.01 to about 5 weight percent of the phosphate ester surfactant based on a total weight of the solution.

The solution contained within the wet wipes of the present invention defines a pH from about 5 to about 8 and desirably from about 5 to about 6. A pH level below about 5 is generally undesirable because the phosphate surfactant precipitates. Whereas, a pH level greater than about 8 is also undesirable and can lead to skin irritation.

The solution may also include a variety of other components which may assist in providing the desired wiping and cleaning properties. For example, the components may include water, emollients, other surfactants, preservatives, chelating agents, pH buffers, fragrances or combinations thereof. The solution may also contain lotions and/or medicaments. To provide reduced skin irritation, the solution desirably includes at least about 80 weight percent water and more desirably at least about 90 weight percent water based on a total weight of the solution.

For example, the solution may include an effective amount of preservative to inhibit the growth of microorganisms. Suitable preservatives are well known to those skilled in the art and may include, for example, parabens, sodiumhydroxymethylglycinate, organic acids such as benzoic and malic acid, DMDM hydantoin and the like and combinations thereof. In a particular embodiment, the preservative is sodium hydroxymethylglycinate which is commercially available from Sutton Laboratories under the trade designation SUTTOCIDE A. The solution may include any amount of the preservatives which provides the desired antimicrobial effect. For example, the solution may include from about 0.1 to about 1.0 weight percent of the preservative based on a total weight of the solution.

The solution may further include additional surfactants which can act as an emulsifier or provide additional cleansing properties. Suitable cosurfactants include, for example, anionic surfactants such as acyl glutamates and acyl isethionates, alkanolamids, amphoteric surfactants, nonionic surfactants and the like or combinations thereof. For example, a suitable acyl glutamate anionic surfactant is potassium cocyl glutamate, a suitable acyl isethionate anionic surfactant is ammonium cocyl isethionate, and suitable amphoteric surfactants include disodium capryloamphdipropionate and disodium cocoamphodiactetate. Suitable nonionic surfactants include diethanolamides having an average of from 12 to 16 carbon atoms, alkylphenol ethoxylates, alcohol ethoxylates, sorbitan esters, glycerol esters and the like. The solution may include any amount of the cosurfactant which provides the improved cleaning or tactile properties. For example, the solution may include from about 0.01 to about 5 weight percent of the cosurfactant based on a total weight of the solution.

In a particular embodiment, the solution of the present invention includes from about 0.01 to about 5.0 and desirably from about 0.1 to about 1.0 weight percent of a nonionic surfactant commercially available from Rhone-Poulenc under the trade designation AKAMULS PSML-20. The addition of such a cosurfactant provides reduced skin irritation and reduced foaming. Such a cosurfactant also acts as an coemulsifier in conjunction with the phosphate.

In another specific embodiment, it has been discovered that the addition of certain cosurfactants such as Lauramide DEA or Cocoamide DEA may provide a broader range of acceptable pH. For example, the addition of Lauramide DEA allowed the acceptable pH range to expand from a range of 6.5 to 8 to a range of from about 5 to about 8. Such an expansion of the acceptable pH range provides improved processability and provides a clear, homogeneous solution. For example, the solution may include Lauramide DEA which is commercially available from Rhone-Poulenc, under the trade designation ALKAMIDE LE. Such a solution may include from about 0.01 to about 5.0 and desirably from about 0.1 to about 1.0 weight percent of said cosurfactant based on a total weight of the solution.

Applicants have discovered that, when compared to conventional wet wipes which have included other types of surfactants, the wet wipes according to the different aspects of the present invention which include a mono alkyl phosphate surfactant have improved tactile properties and cleaning efficacy without excessive levels of skin irritation. Moreover, the wet wipes of the present invention desirably exhibit low levels of foaming for improved performance. The wet wipes also exhibit a lubricious, silky feeling to the user for improved consumer acceptance. The wipes of the present invention further exhibited unexpectedly low levels of eye irritation when subjected to standard product safety tests. This was particularly unexpected since most anionic surfactants generally irritate the eyes.

The wet wipes of the different aspects of the present invention may be manufactured using several different processes well known to those skilled in the art. The particular method and sequence of steps described herein is not a limitation to the present invention, but is disclosed only as one method of producing a wet wipe and stack of wet wipes. Initially, a supply roll of the material being converted into the wet wipes is unwound to provide a continuously moving web of material. The web of material is saturated or otherwise impregnated with the solution of the present invention by any suitable means such as spraying, dipping, or the like as are well known to those skilled in the art. In a particular aspect, the web of material is passed over several perforated tubes which exude the solution into the material.

The web of material is slit in the machine direction into multiple ribbons, each of which may be folded into the type of fold desired for the individual wet wipe. The web of material is slit using a cutter as are well known to those skilled in the art. For example, the web of material can be slit into eight individual ribbons. The ribbons of material are then be folded into a folded configuration such as a z-folded configuration. For example, each ribbon of material may define a top flap portion, a central portion and a bottom flap portion. The top and bottom flap portions are connected to and folded over and under the central portion, respectively to provide the z-folded configuration.

Each folded ribbon may then be combined, one ribbon on top of the other, with the other seven folded ribbons from the same web of material to form a continuous "sausage." The sausage is then cut into "clips" of eight wet wipes apiece and the clips of wet wipes are arranged in a stacked configuration. The number of clips in a stack depends on the desired number of stacks and the number of wet wipes in the final package. For example, for an 80-count package having one stack, ten clips of eight wet wipes apiece would be required to form a single stack of 80 wet wipes. After the stack of wet wipes is property configured, it may be placed in the interior of a container, such as a plastic tub, to provide a package of wet wipes. The container provides a substantially hermetically sealed environment for the wet wipes to minimize the escape of any solution therefrom.

Accordingly, the different aspects of the present invention can advantageously provide wet wipes which, when compared to conventional wet wipes, have improved tactile properties and cleaning while maintaining low levels of skin irritation and foaming. Such wet wipes can advantageously be used for baby wipes, hand wipes, face wipes, cosmetic wipes, household wipes, industrial wipes and the like.

EXAMPLES

The following examples are presented to provide a more detailed understanding of the invention. The particular materials and parameters are exemplary and are not intended to limit the scope of the invention.

Example 1

A particularly suitable solution for the wet wipes of the present invention was prepared according to the following formulation:

| Ingredient CTFA Designation | wt. % |
| --- | --- |
| Water | 98.52 |
| Potassium Laureth mono alkyl phosphate | 0.6 |
| Glycerin | 0.29 |
| Polysorbate-20 | 0.30 |
| Sodium hydroxymethylglycinate | 0.20 |
| Propylparaben | 0.1 |
| Fragrance | 0.05 |

The potassium laureth mono alkyl phosphate was commercially available from Rhone-Poulenc under the trade designation RHODAFAC. The Polysorbate-20 was commercially available from Rhone Poulenc under the trade designation ALKAMULS PSML-20. The sodium hydroxymethylglycinate was commercially available from Sutton Labs, a business having offices located in Catham, N.J., under the trade designation SUTTOCIDE A. Malic acid was then added to the solution to bring the pH level to 5.5. The solution exhibited a silky, lubricious feel and was relatively nonirritating to the skin.

Example 2

A suitable solution for the wet wipes of the present invention was prepared according to the following formulation:

| Ingredient CTFA Designation | wt. % |
| --- | --- |
| Water | 97.02 |
| Potassium Coco mono alkyl phosphate | 0.4 |
| Propylene Glycol | 0.5 |
| Polysorbate-20 | 0.30 |

-continued

| Ingredient CTFA Designation | wt. % |
|---|---|
| Sodium hydroxymethylglycinate | 0.15 |
| Fragrance | 0.03 |

The potassium coco mono alkyl phosphate was commercially available from Rhone-Poulenc under the trade designation RHODAFAC. The Polysorbate-20 was commercially available from Rhone-Poulenc under the trade designation ALKAMULS PSML-20. The sodium hydroxymethylglycinate was commercially available from Sutton Labs, a business having offices located in Chatham, N.J., under the trade designation SUTTOCIDE A. Malic acid was then added to the solution to bring the pH level to 5.5. The solution was cloudy, exhibited a slight silky after feel and precipitated.

Example 3

A suitable solution for the wet wipes of the present invention was prepared according to the following formulation:

| Ingredient CTFA Designation | wt. % |
|---|---|
| Water | 96.85 |
| Potassium Ceteth mono alkyl phosphate | 0.5 |
| Propylene Glycol | 0.5 |
| Sodium hydroxymethylglycinate | 0.15 |

The potassium ceteth mono alkyl phosphate was commercially available from Rhone-Poulenc under the trade designation RHODAFAC. The sodium hydroxymethylglycinate was commercially available from Sutton Labs, a business having offices located in Chatham, N.J., under the trade designation SUTTOCIDE A. Malic acid was then added to the solution to bring the pH level to 5.5. The solution was hazy, and exhibited a slight silky after feel.

Example 4

A suitable solution for the wet wipes of the present invention was prepared according to the following formulation:

| Ingredient CTFA Designation | wt. % |
|---|---|
| Water | 95.0 |
| Potassium Behenyl mono alkyl phosphate | 0.4 |
| Propylene Glycol | 0.5 |
| Polysorbate-20 | 0.30 |
| Sodium hydroxymethylglycinate | 0.20 |
| Propylparaben | 0.1 |
| Fragrance | 0.05 |

The potassium behenyl mono alkyl phosphate was commercially available from Rhone-Poulenc under the trade designation RHODAFAC. The Polysorbate-20 was commercially available from Rhone-Poulenc under the trade designation ALKAMULS PSML-20. The sodium hydroxymethylglycinate was commercially available from Sutton Labs, a business having offices located in Chatham, N.J., under the trade designation SUTTOCIDE A. Malic acid was then added to the solution to bring the pH level to 5.5. The solution was white, cloudy, nonfoaming and lacked a silky after feel.

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A wet wipe comprising a fibrous sheet material and a non-oily aqueous-based solution which includes from about 0.01 to about 10 weight percent based on a total weight of said solution of a phosphate ester surfactant which comprises:

a) a mono alkyl phosphate having the following structural formula:

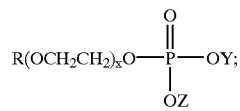

and b) a dialkyl phosphate having the following structural formula:

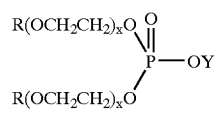

wherein R represents a saturated or unsaturated hydrocarbon group having an average of from 8 to 22 carbon atoms, x represents a number of 0 to 20, and each of Y and Z represents hydrogen, an alkali metal, ammonium or an alkanol amine and wherein a ratio of the mono alkyl phosphate to the dialkyl phosphate is between about 50:50 and about 99:1.

2. A wet wipe according to claim 1 wherein said fibrous sheet material includes a nonwoven material.

3. A wet wipe according to claim 1 wherein said wet wipe includes from about 150 to about 600 weight percent of said solution based on a dry weight of said wet wipe.

4. A wet wipe according to claim 1 wherein a ratio of said mono alkyl phosphate to said dialkyl phosphate is at least about 80:20.

5. A wet wipe according to claim 1 wherein R represents a saturated or unsaturated hydrocarbon group having an average of from 10 to 18 carbon atoms.

6. A wet wipe according to claim 1 wherein R has an average of 12 carbon atoms and is derived from coconut oil.

7. A wet wipe according to claim 1 wherein x represents a number from 0 to 8.

8. A wet wipe according to claim 1 wherein Y is potassium and Z is hydrogen.

9. A wet wipe according to claim 8 wherein said solution further includes from about 0.01 to about 5 weight percent based on a total weight of said solution of a nonionic cosurfactant.

10. A wet wipe according to claim 1 wherein Y is a triethanolamine and Z is hydrogen.

11. A wet wipe according to claim 1 wherein said solution defines a pH of from about 5 to about 8.

12. A wet wipe according to claim 1 wherein said solution includes at least about 80 weight percent water based on a total weight of said solution.

13. A wet wipe according to claim 1 wherein said solution further includes from about 0.01 to about 5 weight percent based on a total weight of said solution of a nonionic cosurfactant.

14. A wet wipe according to claim 1 wherein said phosphate ester surfactant is present in an amount from about 0.01 to about 5 weight percent based on a total weight of said solution.

15. A wet wipe according to claim 1 further comprising from about 0.01 to about 5 weight percent based on a total weight of said solution of a diethanolamide.

16. A wet wipe according to claim 15 wherein the diethanolamide is a Lauramide DEA.

17. A wet wipe according to claim 15 wherein the diethanolamide is Cocamide DEA.

18. A method of using a wet wipe made in accordance with claim 1 comprising using the wet wipe with the solution contained thereon to wipe a human's skin and leaving a solution deposited by using the wet wipe on the human's skin after wiping is completed.

19. A wet wipe comprising a fibrous sheet material and a non-oily aqueous-based solution which includes from about 0.01 to about 10 weight percent based on a total weight of said solution of a phosphate ester surfactant which comprises:

a) a mono alkyl phosphate having the following structural formula:

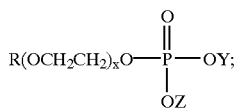

and b) a dialkyl phosphate having the following structural formula:

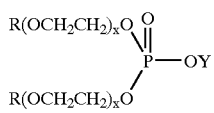

wherein R represents a saturated or unsaturated hydrocarbon group having an average of from 8 to 22 carbon atoms, x represents a number of 1 to 20, and each of Y and Z represents hydrogen, an alkali metal, ammonium or an alkanol amine and wherein a ratio of the mono alkyl phosphate to the dialkyl phosphate is between about 50:50 to about 99:1.

20. A wet wipe according to claim 19 wherein said fibrous sheet material includes a nonwoven material.

21. A wet wipe according to claim 19 wherein said wet wipe includes from about 150 to about 600 weight percent of said solution based on a dry weight of said wet wipe.

22. A wet wipe according to claim 19 wherein the ratio of said mono alkyl phosphate to said dialkyl phosphate is between about 50:50 and about 80:20.

23. A wet wipe according to claim 19 wherein R represents a saturated or unsaturated hydrocarbon group having an average of from 10 to 18 carbon atoms.

24. A wet wipe according to claim 19 wherein R has an average of 12 carbon atoms and is derived from coconut oil.

25. A wet wipe according to claim 19 wherein x represents a number from 0 to 8.

26. A wet wipe according to claim 19 wherein Y is potassium and Z is hydrogen.

27. A wet wipe according to claim 19 wherein Y is a triethanolamine and Z is hydrogen.

28. A wet wipe according to claim 19 wherein said solution defines a pH of from about 5 to about 8.

29. A wet wipe according to claim 19 wherein said solution includes at least about 80 weight percent water based on a total weight of said solution.

30. A wet wipe according to claim 19 wherein said solution further includes from about 0.01 to about 5 weight percent based on a total weight of said solution of a nonionic cosurfactant.

31. A wet wipe according to claim 19 wherein said phosphate ester surfactant is present in an amount from about 0.01 to about 5 weight percent based on a total weight of said solution.

32. A wet wipe according to claim 19 further comprising from about 0.01 to about 5 weight percent based on a total weight of said solution of a diethanolamide.

33. A wet wipe according to claim 32 wherein the diethanolamide is a Lauramide DEA.

34. A wet wipe according to claim 32 wherein the diethanolamide is Cocamide DEA.

35. A wet wipe according to claim 19 wherein the ratio of said mono alkyl phosphate to said dialkyl phosphate is between about 50:50 and about 90:10.

36. A wet wipe according to claim 19 wherein the ratio of said mono alkyl phosphate to said dialkyl phosphate is between about 80:20 and about 99:1.

37. A wet wipe according to claim 19 wherein the ratio of said mono alkyl phosphate to said dialkyl phosphate is between about 80:20 and about 90:10.

38. A method of using a wet wipe made in accordance with claim 19 comprising using the wet wipe with the solution contained thereon to wipe a human's skin and leaving a solution deposited by using the wet wipe on the human's skin after wiping is completed.

39. A wet wipe comprising a fibrous sheet material and an aqueous-based solution which includes from about 0.01 to about 10 weight percent based on a total weight of said solution of a phosphate ester surfactant which comprises:

a) a mono alkyl phosphate having the following structural formula:

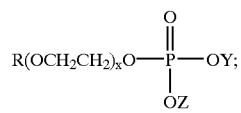

and b) a dialkyl phosphate having the following structural formula:

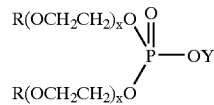

wherein R represents a saturated or unsaturated hydrocarbon group having an average of from 8 to 22 carbon atoms, x represents a number of 1 to 4, and each of Y and Z represents hydrogen, an alkali metal, ammonium or an alkanol amine and wherein a ratio of the mono alkyl phosphate to the dialkyl phosphate is between about 50:50 and about 99:1.

40. A wet wipe according to claim 39 wherein said fibrous sheet material includes a nonwoven material.

41. A wet wipe according to claim 39 wherein said wet wipe includes from about 150 to about 600 weight percent of said solution based on a dry weight of said wet wipe.

42. A wet wipe according to claim 39 wherein a ratio of said mono alkyl phosphate to said dialkyl phosphate is at least about 80:20.

43. A wet wipe according to claim 39 wherein R represents a saturated or unsaturated hydrocarbon group having an average of from 10 to 18 carbon atoms.

44. A wet wipe according to claim 39 wherein R has an average of 12 carbon atoms and is derived from coconut oil.

45. A wet wipe according to claim 39 wherein Y is potassium and Z is hydrogen.

46. A wet wipe according to claim 39 wherein Y is a triethanolamine and Z is hydrogen.

47. A wet wipe according to claim 39 wherein said solution defines a pH of from about 5 to about 8.

48. A wet wipe according to claim 39 wherein said solution includes at least about 80 weight percent water based on a total weight of said solution.

49. A wet wipe according to claim 39 wherein said phosphate ester surfactant is present in an amount from about 0.01 to about 5 weight percent based on a total weight of said solution.

50. A wet wipe according to claim 39 further comprising from about 0.01 to about 5 weight percent based on a total weight of said solution of diethanolamide.

51. A wet wipe according to claim 50 wherein the diethanolamide is a Lauramide DEA.

52. A wet wipe according to claim 50 wherein the diethanolamide is Cocamide DEA.

53. A method of using a wet wipe made in accordance with claim 39 comprising using the wet wipe with the solution contained thereon to wipe a human's skin and leaving a solution deposited by using the wet wipe on the human's skin after wiping is completed.

* * * * *